United States Patent [19]

Polaschegg

[11] Patent Number: 5,057,076
[45] Date of Patent: Oct. 15, 1991

[54] INFUSION APPARATUS

[75] Inventor: Hans D. Polaschegg, Oberursel, Fed. Rep. of Germany

[73] Assignee: Fresenius AG, Bad Homburg van der Hohe, Fed. Rep. of Germany

[21] Appl. No.: 604,961

[22] Filed: Oct. 29, 1990

[30] Foreign Application Priority Data

Nov. 29, 1989 [DE] Fed. Rep. of Germany ....... 3939247

[51] Int. Cl.$^5$ ............................................. A61M 31/00
[52] U.S. Cl. .............................. 604/67; 128/DIG. 13
[58] Field of Search ..................... 604/131, 65, 67, 66; 128/DIG. 13

[56] References Cited

U.S. PATENT DOCUMENTS

| | | | |
|---|---|---|---|
| 3,841,799 | 10/1974 | Spinosa | 417/477 |
| 4,094,318 | 6/1978 | Burke et al. | 604/65 |
| 4,187,057 | 2/1980 | Xanthopoulos | 417/63 |
| 4,501,531 | 2/1985 | Bilstad et al. | 604/67 |
| 4,657,529 | 4/1987 | Prince et al. | 128/DIG. 13 |
| 4,710,166 | 12/1987 | Thompson et al. | 604/65 |
| 4,828,545 | 5/1989 | Epstein et al. | 604/68 |
| 4,966,579 | 10/1990 | Polaschegg | 604/65 |

FOREIGN PATENT DOCUMENTS 7913478 10/1979 Fed. Rep. of Germany .
3329977 8/1985 Fed. Rep. of Germany .

Primary Examiner—Paul J. Hirsch
Attorney, Agent, or Firm—Marshall, O'Toole, Gerstein, Murray & Bicknell

[57] ABSTRACT

This invention relates to an apparatus for dosed, continuous and simultaneous infusion operations. To prevent an uncontrolled flow through the conveying conduits, which can above all occur during the installation of a flexible tube into or its removal from a peristaltic pump due to the action of gravity, the invention provides a valve (5, 6) which is positioned in the conveying conduit of the peristaltic pump and operatively connected to a door detector of the pump in such a way that the valve is closed when the door is opened, and opened when the door is closed.

10 Claims, 2 Drawing Sheets

INFUSION APPARATUS

BACKGROUND OF THE INVENTION

This invention relates to an apparatus for the dosed, continuous and simultaneous infusion of several infusion solutions or medicament solutions in accordance with the preamble of the main claim.

During the infusion of medicament solutions or infusion solutions, specific volume quantities are supplied to a patient at a given time unit by operating an infusion pump. For reasons of operational reliability and for the patient,s medical safety, the amount of solution to be supplied must strictly be adhered to. High demands are therefore made on the technical safety equipment of such an apparatus.

Under certain conditions the volume amount to be respectively supplied to a patient must strictly be observed, i.e both an increase in and a reduction of the amount must be prevented. As a result of these requirements, the technical equipment is very complicated and expensive. The attempt has therefore been made to somewhat lower the requirements and to simplify the construction of the whole safety equipment. With specific kinds of solutions to be supplied to a patient, or with specific medical indications, a solution amount smaller than the predetermined solution amount to be supplied to a patient is acceptable. The resultant medical risk is considered to be small, as the supply of a reduced amount can be easily detected and compensated for in routine checks carried out by the operating personnel or with the aid of other technical monitoring possibilities. Hence, it is possible to compensate for the effects caused by the supply of a reduced amount by taking specific measures within a greater time interval.

By contrast, many applications strictly forbid the uncontrolled supply of excess amounts of solutions to be administered to a patient. The delivery of excess amounts may be due to technical defects in the apparatus or may result from typical operating mistakes made by the personnel. While technical defects in the apparatus can be detected with the aid of a flow meter and the system can be shut off in emergency cases, or an alarm signal may be given, additional constructional steps must be taken for preventing operating errors.

During operation risks arise especially at the beginning, during an intended interruption or upon completion of the infusion process. If there is a free passage of the corresponding flexible tubes or catheters in these operational states, an uncontrolled amount of infusion solution may flow into the patient,s body due to the action of gravity. This danger exists when an infusion conduit is put into the infusion pump at the beginning of the infusion step. It also exists when the infusion process is interrupted or stopped or when the infusion conduit is to be removed from the pump at the same time.

German Utility Model 79 13 478 shows an infusion pump where a mechanical safety system is provided in the area of the door mounted on the housing for preventing the door from being closed as long as the flexible tube is not completely and correctly positioned. This mechanical system merely prevents the closing of the door, but is not capable of detecting an unintended opening of the door. In the last-mentioned case the flexible tube may come loose and slip out while the pump is operated. German patent application 33 29 977 published Mar. 7, 1985 discloses a multi-infusion arrangement wherein a valve is respectively arranged after a supply reservoir. Downstream of the valve, a conduit is guided to one common infusion pump which conveys all fluid flows from the supply reservoirs to a patient. Although it is here possible to close the feed line between the supply reservoir and the common infusion pump by means of the individual valves, fluid can freely flow to the patient when the pump is unintentionally opened, as there are no shut-off mechanisms.

OBJECT UNDERLYING THE INVENTION

It is the object of this invention to provide an apparatus of the above-mentioned type which is of a simple construction and can be operated in a reliable way and nevertheless excludes the possibility of an unintended supply of one or several infusion solutions to a patient.

INVENTIVE SOLUTION

This object is attained through the combined features of the main claim. The subclaims show advantageous developments of the invention.

DESCRIPTION OF THE INVENTION

The apparatus of the invention offers a number of considerable advantages. While the pump mechanism of the infusion pump prevents any free flow through the infusion conduit in the inserted state of the infusion conduit and thus acts as a valve, the infusion conduit is no longer blocked or interrupted by the pump mechanism when being removed from the pump. Normally, a manually operable clamp is therefore provided for closing the infusion conduit. When the infusion conduit is inserted into the pump mechanism, said manual clamp can be opened without the risk of an excess amount being conveyed, as the pump mechanism itself acts as a shut-off valve. Whenever the infusion conduit is removed from the infusion pump by the operating personnel, it is necessary in the prior art to first close the manual clamp and then to remove the conduit. In cases where the manual clamp is not closed or only partly closed, the infusion solution inside the infusion container flows in an uncontrolled way through the infusion conduit into the patient's body.

Hence, the apparatus of the invention has the advantage that the infusion conduit or conveying conduit can be released independently of the operation of the manual clamp, so that the operational safety of the apparatus cannot be affected by manipulations of the operating personnel.

The devices known from the prior art include a mechanism which only releases the cross-section of the infusion conduit or passage conduit after two operational steps. An alarm signal is normally given between the two operational steps to draw the personnel's attention to a possible risk. However, the infusion conduit is not forcedly closed, so that operating mistakes cannot be entirely ruled out. It should here be pointed out that such operations are often carried out by semi-skilled or less expert persons and that especially in cases of emergency there is often not enough time to check the individual operational steps once again. The devices known from the prior art are thus not safe and might present a risk.

The apparatus of the invention is especially advantageous in multi-infusion systems. In these systems a manual operation of the clamps or a corresponding monitoring of the individual handling steps is considerably more difficult on account of the combination of a plurality of infusion pumps, resulting in a complicated technical apparatus. With the invention, it is possible to actuate the valve already provided in the conveying conduit by means of a relatively simple safety mechanism or to provide an additional valve of simple construction. The whole apparatus is thus as reliable as possible from an operational point of view and cannot be affected by misoperations, as the door detector of the peristaltic pump automatically detects the opening or closing of the door. A special advantage of the invention consists in that no additional failure-prone safety means are required and that e.g. no other flow sensors or similar means have to be provided, which means make the manufacture of the whole system more expensive.

In a preferred embodiment of the invention the valve is electrically actuable. As an alternative, it is also possible to actuate the valve in a mechanical way. Both embodiments are of advantage. With a mechanical actuation it is possible to couple the valve and/or the actuation mechanism directly with the door of the pump, while an electrical actuation offers the possibility of arranging the valve at a greater distance from the pump.

When the valve is mechanically actuable, it can be integrated into the pump and is then directly actuable by means of the door.

It is especially advantageous to design a mechanically actuable valve in the form of a spring element which in the opened state of the door, i.e. without the application of a force, clamps off the conveying conduit or the infusion conduit. When the door is closed, the spring element can e.g. be expanded, so that the flexible tube is released and the flow passage is thus not impaired.

It has been found to be especially advantageous when the spring element rests on an abutment at the side facing away from the door. With this construction no additional lifting mechanisms or the like are required, but the door itself acts as an actuation lever for the spring element.

When the valve is electrically actuated, it is especially advantageous when it is in the closing position in the currentless state because even in the case of a sudden voltage drop or an interruption of the power supply the infusion solution cannot flow in an uncontrolled way into the patient's conduit. For the actuation of the valve the door detector may e.g. be electrically connected via the control unit to the valve, so that a suitable pulse is given for opening or closing the valve.

The apparatus of the invention allows various modifications of the valve. It is e.g. possible to form the valve integrally with the valve arranged in the conveying conduit, i.e. to use the valve of the conveying conduit as both a safety valve together with the flow sensor and a safety valve during the opening of the door of the pump. Alternatively, it is also possible to design the valve as a separate valve to be e.g. installed at another place of the conduit arrangement of the conveying conduits.

DESCRIPTION OF A PREFERRED EMBODIMENT OF THE INVENTION

Figure 1:
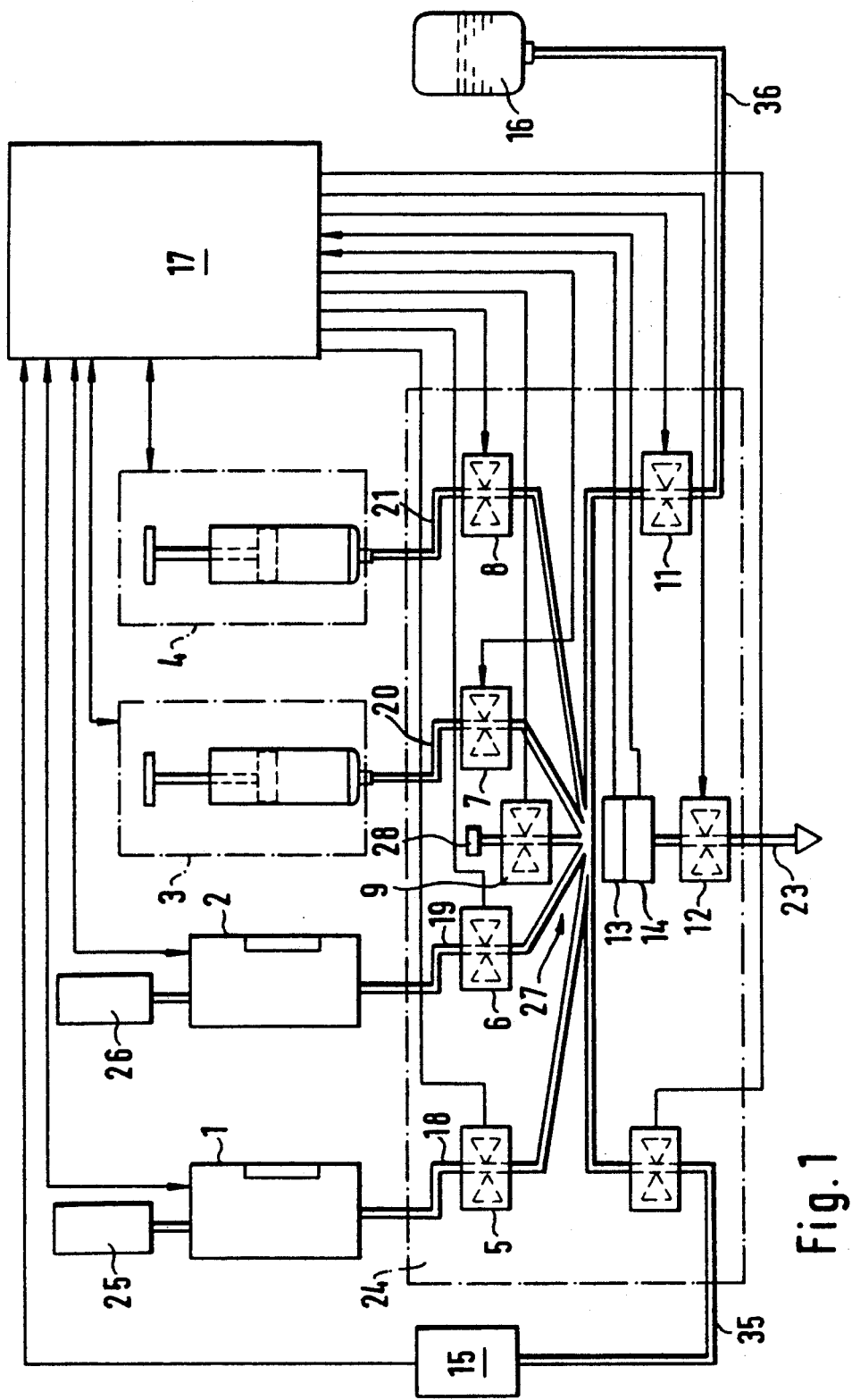
Figure 2:
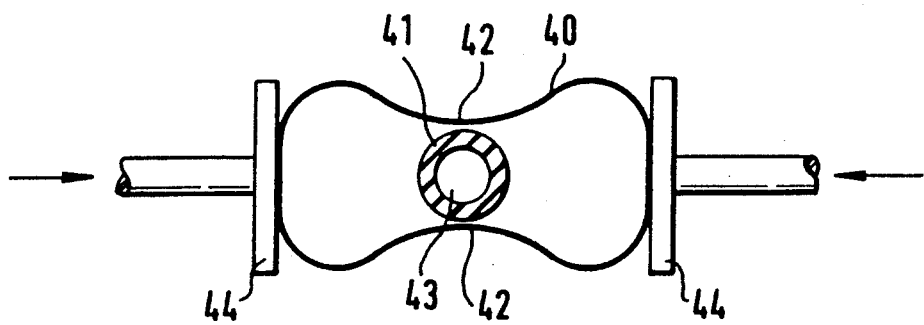
Figure 3:
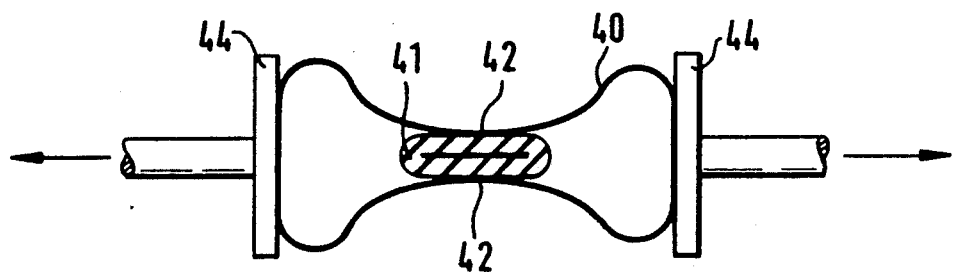

A preferred embodiment of the invention shall now be described with reference to the drawing, in which FIG. 1 is a schematic view of a multi-infusion device;

FIG. 2 is a schematic view of a valve construction of the the invention in the opened state; and FIG. 3 is a schematic view of the valve construction shown in FIG. 2, but in the closed state.

The multi-infusion means shown in FIG. 1 comprises two linear peristaltio infusion pumps 1 and 2, two injeotion infusion pumps 3 and 4, a gravitational-force infusion means 16 and a CVD measuring means 15. Infusion pumps 1 and 2 are respectively connected to an infusion container 25 and 26. Each of infusion pumps 1 and 2 as well as gravitational-force infusion means 16 are connected to respective conveying conduits designated by reference numerals 18, 19, 20, 21 and 36. Each of said conveying conduits has positioned therein a clamping valve 5, 6, 7, 8, and 11, respectively, the valves being signalwise connected to a computing and controlling unit 17. This unit is simultaneously connected to pumps 1, 2, 3 and 4 for controlling the same in accordance with a given program. Conveying conduits 18, 19, 20 and 21, feed line 35 to CVD measuring means 15, and conveying conduit 36 of the gravitational-force infusion means are jointly connected via a transition member 27 to a patient's conduit 23. An air sensor 13 and a flow sensor 14 are provided in said conduit 23. Another valve 12 is arranged downstream of the flow sensor. Air sensor 13, flow sensor 14 and valve 12 are also connected to computing and controlling unit 17.

An aerating means 28 is additionally mounted on transition member 27 and operable through a valve 9 which is also connected to computing and controlling unit 17. There may also be provided a hydrophobic filter and a check valve (not shown) for said aerating means.

The different infusion means can thus be operated with the aid of controlling and computing unit 17, the respective valves offering the possibility of supplying specific amounts of infusion solution. Safety valve 12 may be closed if the delivery rate does not correspond to the desired values.

The two peristaltic pumps 1 and 2 are of a conventional construction and comprise a rotor with pressure rolls which js inserted in a tube bend. The pump is here equipped with a door which provides access to the pump chamber for inserting or withdrawing the flexible tube. A safety means which is schematically shown in FIGS. 2 and 3 and forms a valve is mounted in the area of the door of pumps 1 and 2.

A spring element 40 which surrounds a flexible tube 41 is provided in the embodiment illustrated in FIGS. 2 and 3. Spring element 40 is of a substantially annular configuration and comprises inwardly projecting noses 42 at two opposite sides. In the unloaded initial position of spring element 40, as shown in FIG. 3, the two noses 42 press against each other and squeeze flexible tube 41, so that its lumen 43 is pressed and thus closed.

Next to spring element 40, there are plates 44 which are connected to a mechanism (not described in detail) which may be of a mechanical or electrical type. Plates 44 can be moved towards and away from each other.

As shown in FIG. 2, spring element 40 may be pressed laterally by means of pressure plates 44, so that the two noses 42 move away from each other and release flexible tube 41.

The invention is not to be understood as restricted to the embodiment shown. Rather, many changes and modifications may be made by those skilled in the art without departing from the spirit and scope of the invention.

I claim:

1. An apparatus for the dosed, continuous and simultaneous infusion of a plurality of infusion solutions or medicament solutions, comprising at least one pump (1, 2) respectively provided with a housing and a door, conveying conduits (18-21) which pass from containers containing said infusion solutions or medicament solutions and are connected via a transition member to a common patient's conduit (23), valves (5-12) provided in each of said conveying conduits, a flow sensor (14) provided in said patient's conduit (23) for sensing the flow rate, and a control unit operatively connected to said valves (5-12), said pump (1, 2) and said flow sensor (14), said flow sensor (14) being arranged downstream of said pump, and said control unit initiating the closure of said valves (5-12) upon detection of a fluid stop by said flow sensor (14), characterized in that a said valve (5, 6) provided in said conveying conduit of a said peristaltic pump (1, 2) is operatively connected to a door detector of said associated pump (1, 2) in such a way that said valve (5, 6) is closed when said door is opened, and opened when said door is closed.

2. An apparatus according to claim 1, characterized in that said valve (5, 6) is electrically actuable.

3. An apparatus according to claim 1, characterized in that said valve (5, 6) is mechanically actuable.

4. An apparatus according to claim 3, characterized in that said valve is integrated into said pump and actuable by means of said door.

5. An apparatus according to claim 3 or 4, characterized in that said valve (5, 6) consists of a spring element (40) which clamps off said conveying conduit in the opened state of said door and can be expanded for releasing said conveying conduit when said door is closed.

6. An apparatus according to claim 5, characterized in that said spring element (40) rests on an abutment at the side facing away from said door.

7. An apparatus according to claim 1 or 2, characterized in that said valve (5, 6) is an electrically switchable valve which is in the closed position in the currentless state.

8. An apparatus according to claim 7, characterized in that said door detector is connected to said valve (5, 6) via said control unit.

9. An apparatus according to claim 1, characterized in that said valve (5, 6) is integrally formed with said valve arranged in said conveying conduit.

10. An apparatus according to claim 1, characterized in that said valve (5, 6) is formed as a separate valve.

* * * * *